United States Patent [19]

Endo

[11] 4,396,602
[45] Aug. 2, 1983

[54] BLOOD GLUCOSE LEVEL LOWERING AGENTS
[75] Inventor: Akira Endo, Tokyo, Japan
[73] Assignee: Asahi Kasei Kogyo Kabushiki Kaisha, Osaka, Japan
[21] Appl. No.: 304,467
[22] Filed: Sep. 22, 1981
[51] Int. Cl.³ .............................................. A61K 37/48
[52] U.S. Cl. ...................................................... 424/94
[58] Field of Search .......................................... 424/94
[56] References Cited
U.S. PATENT DOCUMENTS
4,083,960  4/1978  Yamashita et al. .................. 424/94
4,150,116  4/1979  Taubman et al. ..................... 424/94
4,255,414  3/1981  Lembke et al. ...................... 424/94

Primary Examiner—Sam Rosen
Attorney, Agent, or Firm—Sughrue, Mion, Zinn, Macpeak & Seas

[57] ABSTRACT

A method of lowering the blood glucose level in mammals and a blood glucose level-lowering agent are described. The method comprises administering an enzyme capable of synthesizing sparingly-digestible saccharides from easily-digestible saccharides. The blood glucose level-lowering agent comprises the enzyme capable of synthesizing sparingly-digestible saccharides from easily-digestible saccharides and a glucosidase-inhibiting agent.

12 Claims, No Drawings

BLOOD GLUCOSE LEVEL LOWERING AGENTS

FIELD OF THE INVENTION

The present invention relates to a method of lowering the blood glucose level and a blood glucose level-lowering agent (hypoglycemic agent).

BACKGROUND OF THE INVENTION

Recently, metabolic diseases, such as diabetes, obesity and arteriosclerosis, resulting from an increase in a blood glucose level due to excessive intake of digestible saccharides, particularly starch and sucrose, have been increasing. Such unbalanced eating habits of intaking digestible saccharides are also responsible for digestive diseases, such as diarrhea, gastroenteric catarrh and abnormal zymosis in the bowel.

Completely satisfactory drugs for these diseases have not yet been discovered, and it has long been desired to develop improved drugs.

SUMMARY OF THE INVENTION

It has now been discovered that an enzyme capable of synthesizing sparingly-digestible saccharides, such as polysaccharides and oligosaccharides (e.g., cyclodextrin), from easily-digestible saccharides, such as monosaccharides, oligosaccharides (e.g., dextrin, maltose, isomaltose and sucrose) and polysaccharides, lowers blood glucose levels in mammals including human beings, and has excellent effects in preventing and treating metabolic and digestive diseases.

As a result of an extensive search for a substance having a blood glucose level-lowering activity, it has further been discovered that when an enzyme capable of synthesizing sparingly-digestible saccharides from easily-digestible saccharides is used in combination with a glucosidase-inhibiting agent which has already been known to have the effect of lowering a blood glucose level, the blood glucose level-lowering effect is enhanced synergistically compared to when they are used separately.

Thus, the present invention provides, in one embodiment, a method of lowering the blood glucose level in mammals comprising orally administering an enzyme capable of synthesizing sparingly-digestible saccharides from easily-digestible saccharides, and in another embodiment, a blood glucose level-lowering agent containing an enzyme capable of synthesizing sparingly-digestible saccharides from easily-digestible saccharides and a glucosidase-inhibiting agent.

DETAILED DESCRIPTION OF THE INVENTION

Enzymes which can be used in the invention, i.e., having the ability to synthesize sparingly-digestible saccharides from easily-digestible saccharides include:

Dextransucrase, produced by the genera Leuconostoc, Streptococcus, and Betabacterium, which synthesizes dextran from sucrose; Dextran 6-glycociltransferase, produced by the genus Acetobacter, which synthesizes dextran from amylodextrin; Levansucrase, produced by the genera Bacillus, Acetobacter, Pseudomonas, and Xanthomonas, which synthesizes levan from sucrose; Amylomaltase, produced by the genus Escherichia, which synthesizes amylose from maltose; Amylosucrase, produced by the genus Neisseria, which synthesizes amylopectin-like polysaccharide from sucrose; and cyclodextrin-synthesizing enzymes, produced by the genera Bacillus and Klebsiella, which synthesize cyclodextrin ($\alpha$, $\beta$, and $\Gamma$ types) from starch or sucrose. Of these enzymes, dextransucrase and cyclodextrin-synthesizing enzymes are particularly preferred. These enzymes are all known and can be prepared by known procedures (e.g., W. Pigman and D. Horton, Ed., *The Carbohydrates. Chemistry and Biochemistry*, Academic Press, pp. 302–373 (1970); S. P. Colowick and N. O. Kaplan, Ed., *Methods in Enzymology*, Academic Press, Vol. 1, pp. 178–192 (1955), and Vol. 5, pp. 140–155 (1962); E. F. Neufeld and V. Ginsberg, Ed., *Methods in Enzymology*, Vol. 8, pp. 500–505 (1966); T. J. Montville et al., *Advances in Applied Microbiology*, Academic Press, Vol. 24, pp. 55–84 (1978); H. Horikoshi and N. Nakamura, *Kagaku to Seibutsu*, Vol. 17, pp. 300–305 (1979); K. Matsuda and M. Kobayashi, *Hakko to Kogyo*, Vol. 36, pp. 11–21 (1978); S. Kobayashi and K. Kainuma, *Hakko to Kogyo*, Vol. 36, pp. 176–183 (1978); and T. Tanaka, S. Oi, M. Iizuka, and T. Yamamoto, *Agric. Biol. Chem.*, Vol. 42, pp. 323–326 (1978)).

In addition, various polysaccharide-synthesizing enzymes or enzyme systems produced by bacteria, yeast and fungi, which synthesize sparingly-digestible polysaccharides (e.g., cellulose, pullulan, nigeran, $\beta$-glucans and curdrun), can be used in the invention. Furthermore, enzymes synthesizing polysaccharides of plants, such as hemi-cellulose, pectin, and rubber-like polysaccharides; enzymes synthesizing various seaweed polysaccharides; and animal enzymes synthesizing mucopolysaccharides (see. A. Harada and A. Misaki, Sogo Tatorui Kagaku, Kodansha, Japan, pp. 3–436 (1974)) can be used in the invention.

These enzymes may be used in either purified or crude form. Furthermore, either dead cells or living cells containing these enzymes can be used. The toxicity of these enzymes is very low ($LD_{50}$:>1 g/kg mice, P.O.).

The glucosidase-inhibiting agent which is used in the other embodiment of the invention inhibits the amylase, sucrase and maltase actions. Examples of such glucosidase-inhibiting agents include Bay g 5421, TAI, S-AI, S-GI, Haim, Nozilimycin, and Tris. These glucosidase-inhibiting agents are known and can be prepared by the known methods (see D. D. Schmidt, W. Frommer, B. Junge, L. Muller, W. Wingender and E. Truscheit, *Naturwissenschaften*, Vol. 64, pp. 535–536 (1977); S. Namiki, K. Kamikori, T. Nagate, K. Sugita, H. Hara, E. Mori, S. Omura and M. Ozeki, *Denpun Kagaku*, Vol. 26, pp. 134–144 (1979) and Vol. 27, p. 107 (1980); S. Murao, K. Oyama, H. Murai, A. Goto, Y. Matsui, K. Fukuhara, S. Miyata, M. Sumida and M. Aria, Denpun Kagaku, Vol. 26, pp. 157–164 (1979); S. Ueda, Y. Kiba and H. Sain, *Denpun Kagaku*, Vol. 26, pp. 145–156 (1979); T. Niwa, T. Tsuruoka, S. Inoue and T. Niida, *Amylase Symposium*, Vol. 7, p. 91 (1972); W. Puls and U. Keup, *Metabolism*, Vol. 24, pp. 93–98 (1974); S. Murao and K. Ohyama, *Agric. Biol. Chem.*, Vol. 39, p. 2271 (1975); S. Murao and K. Ohyama, *Agric. Biol. Chem.*, Vol. 41, pp. 919 and 2221 (1977); S. Murao and S. Miyata, Agric. Biol. Chem., Vol. 44, p. 219 (1980); S. Murao, A. Goto, Y. Matsui and K. Ohyama, *Agric. Biol. Chem.*, Vol. 44, p. 1679 (1980); and T. Niwa, S. Inoue, T. Tsuruoka, Y. Koaze and T. Niida, *Agric. Biol. Chem.*, Vol. 34, p. 966 (1970)).

These glucosidase-inhibiting agents may be used in either purified or crude form. The toxicity of these inhibiting agents is very low (LD$_{50}$: >500 mg/kg, mice, P.O.).

Where the enzyme capable of synthesizing sparingly-digestible saccharides from easily-digestible saccharides is used in combination with the glucosidase-inhibiting agent, the composition ratio can be varied within a wide range. It is most preferred, however, that the weight ratio of the enzyme to the glucosidase-inhibiting agent is from 1/20 to 20/1.

The blood glucose level-lowering agent used according to the invention is either the enzyme alone, or a combination of the enzyme and the glucosidase-inhibiting agent, which can be prepared simply by mixing them. The blood glucose level-lowering agent can be converted into a powder, a capsule, a tablet or the like, along with suitable excipients. Furthermore, it may contain a stabilizer. Moreover, it can be used in combination with other agents to prevent and treat metabolic and digestive diseases.

The blood glucose level-lowering agent of the invention can be administered orally, intaperitoneally, or intravenously. In general, oral administration is suitable. Although the amount of the blood glucose level-lowering agent (the enzyme alone or a mixture of the enzyme and the glucosidase-inhibiting agent) being administered varies depending on the type of disease, extent, and so forth, it is usually from about 0.2 to 2,000 mg/day, and in particular, it is preferred that the blood glucose level-lowering agent is administered orally in an amount of 1 to 100 mg/day.

Hereinafter, the invention is described in greater detail by reference to the following examples.

EXAMPLE 1

(i) A dextransucrase-producing strain, *Leuconostoc mesenteroides* NRRL B-1299, was aerobically cultivated at 26° C. for 24 hours by the use of a culture medium containing 2% of sucrose, 2% of corn steep liquor, 0.2% of K$_2$HPO$_4$, 0.01% of MgSO$_4$.7H$_2$O, 0.001% of FeSO$_4$.7H$_2$O, 0.001% of MnCl.4H$_2$O, and 0.001% of NaCl, and having a pH of 7.4. After the cultivation was completed, the medium was filtered to separate it into a filtrate and a solid fraction.

Solid ammonium sulfate was added to a part of the filtrate with stirring at room temperature to 30% saturation, followed by further stirring for 30 minutes. Precipitates formed were collected by centrifugation and discarded. Thereafter, to the resulting liquid was added ammonium sulfate to 70% saturation, and precipitates thus formed were collected by centrifugation. The precipitates were dissolved in a 0.01 M phosphate buffer at pH 6.7, dialyzed overnight against the buffer and freeze-dried to obtain Enzyme A. A part of the remaining filtrate was directly freeze-dried to obtain a crude enzyme (Enzyme B).

A part of the solid fraction was treated with acetone at low temperatures to obtain an acetone-dried cell fraction (Enzyme C). The remaining solid fraction was ground along with silica sand at a low temperature and was subjected to high-speed centrifugal separation. The supernatant liquid was withdrawn and freeze-dried to obtain Enzyme D.

(ii) Male ICR mice (18 to 21 g) were divided into groups of five mice, deprived of food for 24 hours and orally administered with 2.5 g/kg of sucrose. At the same time, each of the above prepared enzymes was orally administered in an amount of 100 mg/kg. After 15 minutes, 30 minutes, 1 hour and 3 hours, blood samples were collected, and the blood glucose level was determined. The results are shown in Table 1.

It can be seen from Table 1 that with the groups to which Enzymes A, B, C and D were administered, the blood glucose level was markedly reduced compared with the control group to which sucrose alone was administered. The values in Table 1 are average values for each group of five mice.

TABLE 1

| | Blood Glucose Level (mg/dl) | | | |
|---|---|---|---|---|
| Group | After 15 Min. | After 30 Min. | After 1 Hr. | After 3 Hr. |
| Control | 291 | 226 | 183 | 152 |
| Group administered with Enzyme A | 138 | 157 | 121 | 129 |
| Group administered with Enzyme B | 169 | 183 | 139 | 135 |
| Group administered with Enzyme C | 196 | 206 | 167 | 136 |
| Group administered with Enzyme D | 170 | 181 | 160 | 133 |

EXAMPLE 2

(i) A Levansucrase-producing strain, *Bacillus subtilis* BS. 5 (stored by Dr. Delaporte (PCB, Paris, France)), was cultivated on a culture medium comprising sucrose 6%, 0.1 M KNO$_3$, 0.07 M K$_2$HPO$_4$, 0.3 M KH$_2$PO$_4$, 0.5 mM MgSO$_4$, 0.05 mM Fe$_2$(SO$_4$)$_3$, 0.05 mM ZnSO$_4$, 0.01 M MnSO$_4$, and 1 mM CaCl$_2$ at 30° C. under aerobic conditions. The cultivation was stopped after 48 hours, and a filtrate was obtained by filtration. The pH of the filtrate was adjusted to 5.5, and an equal amount of acetone was added thereto while stirring and cooling.

Precipitates formed were collected by centrifugal separation, fully washed with acetone, and dried to obtain a dry powder (Enzyme E).

(ii) The influences of Enzyme E on the blood glucose level was examined by the same method as in Example 1. The results are shown in Table 2.

It can be seen from Table 2 that the group administered with Enzyme E showed a marked reduction in the blood glucose level compared with the control group.

TABLE 2

| | Blood Glucose Level (mg/dl) | | | |
|---|---|---|---|---|
| Group | After 15 Min. | After 30 Min. | After 1 Hr. | After 3 Hr. |
| Control | 291 | 226 | 183 | 152 |
| Group administered with Enzyme E | 162 | 182 | 169 | 148 |

EXAMPLE 3

(i) An Amylosucrase-producing strain, *Neisseria Perflava* 19-34 (stored by H. J. Hehre (Albert Einstein College of Medicine, New York, N.Y., U.S.A.)), was cultivated aerobically on a culture medium comprising glucose 0.5%, peptone 1%, sodium citrate 0.15%, yeast extract 0.02%, KH$_2$PO$_4$ 0.05%, and Na$_2$HPO$_4$ 0.15% at 37° C. for 5 days. After the cultivation, an extract containing no cell was obtained and treated with ammonium sulfate to obtain a fraction. The thus-obtained fraction was freeze-dried to obtain Enzyme F.

(ii) The blood glucose level-lowering effect of Enzyme F was examined by the same method as in Example 1. The results are shown in Table 3. As can be seen from Table 3, a significant effect was observed.

TABLE 3

| Group | Blood Glucose Level (mg/dl) | | | |
|---|---|---|---|---|
| | After 15 Min. | After 30 Min. | After 1 Hr. | After 3 Hr. |
| Control | 291 | 226 | 183 | 152 |
| Group administered with Enzyme F | 246 | 196 | 168 | 139 |

EXAMPLE 4

(i) A cyclodextrin-synthesizing enzyme-producing strain, Bacillus macerans ATCC 8514, was cultivated on a culture medium (pH 6.5) comprising oatmeal 5%, $(NH_4)_2HPO_4$ 0.3%, $Na_2SO_4$ 0.2%, and KCl 0.04%, and small amounts of chlorides of Mg, Ca, Mn, Fe (trivalent), Zn and Co at 37° C. for 15 hours under aerobic conditions. The cultivation filtrate was concentrated to 1/10 of the original volume thereof, and an equal amount of acetone was added thereto while cooling. Precipitates formed were collected, dissolved in a small amount of water, and freeze-dried to obtain Enzyme G.

(ii) The blood glucose level-lowering effect of Enzyme G was examined by the same method as in Example 1 with the exception that 1 g/kg of starch was used in place of the sucrose. The results are shown in Table 4. As can be seen from Table 4, a significant effect was observed.

TABLE 4

| Group | Blood Glucose Level (mg/dl) | | | |
|---|---|---|---|---|
| | After 15 Min. | After 30 Min. | After 1 Hr. | After 3 Hr. |
| Control | 221 | 206 | 159 | 136 |
| Group administered with Enzyme G | 166 | 158 | 134 | 132 |

EXAMPLE 5

A bacterial strain having the ability to produce a cyclodextrin-synthesizing enzyme, Bacillus sp. ATCC 21783, was cultivated on a culture medium comprising soluble starch 2%, peptone 0.5%, yeast extract 0.5%, $K_2HPO_4$ 0.1%, $MgSO_4.7H_2O$ 0.02%, and $Na_2CO_3$ 1% at 37° C. for 3 days under aerobic conditions. The cultured broth was filtered to obtain a filtrate. To the thus obtained filtrate was added cold acetone to form precipitates. The precipitates were collected and freeze-dried to obtain a crude enzyme (Enzyme H). The blood glucose level-lowering effect of Enzyme H was examined by the same method as in Example 4. The results are shown in Table 5. As can be seen from Table 5, a significant effect was observed.

TABLE 5

| Group | Blood Glucose Level (mg/dl) | | | |
|---|---|---|---|---|
| | After 15 Min. | After 30 Min. | After 1 Hr. | After 3 Hr. |
| Control | 221 | 206 | 159 | 136 |
| Group administered with Enzyme H | 159 | 142 | 133 | 129 |

EXAMPLE 6

A control group (five mice) of DDYF male mice was bred for 2 weeks with a test food comprising sucrose 69.9%, casein 20%, olive oil 5%, an inorganic salt mixture 4%, a vitamin mixture 1%, and choline chloride 0.1%. On the other hand, a test group (five mice) was administered with Enzyme B prepared in Example 1 in an amount of 100 mg/kg/day while breeding with the same test food as used above.

After 2 weeks, blood samples were collected, and the amount of neutral fat in serum was determined by the usual method as described in I. Kanai and M. Kanai, Rinsho Kensaho Teian, Kinbara Shuppan, Edit. 27, VII-66 (1975). With the control group, the amount was 218 mg/dl, whereas with the test group, 136 mg/dl, and it can thus be seen that the value is markedly reduced by the administration of Enzyme B. (The values are average values for each group of five mice.)

EXAMPLE 7

(i) A dextransucrase-producing strain, Streptococcus mutans 20623 (FERM-BP No. 57), was inoculated on a brain heart infusion broth "Eiken" (produced by Eiken Kagaku Co., Ltd.) and aerobically cultivated thereon at 37° C. for 18 hours. After the cultivation was completed, the cultured broth was filtered to obtain a filtrate. The thus-obtained filtrate was adjusted to 60% saturation by adding ammonium sulfate. Precipitates formed were collected by centrifugation. The precipitates were then dissolved in a 0.01 M phosphate buffer at pH 6.7, dialyzed overnight against the buffer and freeze-dried to obtain Enzyme I.

(ii) Male wistar rats (142 to 151 g) (groups of six rats) were deprived of food for 24 hours. Enzyme I was orally administered in an amount of 10 mg/kg, and, at the same time, sucrose was orally administered in an amount of 2 g/kg. 30 minutes after the administration, blood samples were collected and the blood glucose level was measured.

With the control group to which sucrose alone was administered, the blood glucose level was 171 mg/dl, whereas the blood glucose level of the test group to which Enzyme I was administered was markedly reduced to 127 mg/dl (an average blood glucose value for each group of six rats).

EXAMPLE 8

(i) A dextransucrase-producing strain, Streptococcus salivarius IFO 13956, was inoculated on a brain heart infusion broth "Eiken" and aerobically cultivated thereon at 37° C. for 18 hours. After the cultivation was completed, the cultivated broth was filtered to obtain a filtrate. The thus-obtained filtrate was adjusted to 60% saturation by adding ammonium sulfate. Precipitates thus-formed were collected, dialyzed with a 0.01 M phosphate buffer, and freeze-dried to obtain Enzyme J.

The blood glucose level-lowering effect of Enzyme J was determined by the same method as in Example 7 with the exception that the amount of Enzyme J administered was changed to 30 mg/kg. With the control group to which sucrose alone was added, the blood glucose level after 30 minutes was 172 mg/dl, whereas the blood glucose level of the group to which Enzyme J was administered was significantly reduced to 138 mg/dl (an average blood glucose value for each group of six rats).

EXAMPLE 9

(i) A cyclodextrin-synthesizing enzyme-producing strain, Bacillus macerans 17011 (FERM-BP No. 56), was inoculated on a culture (pH 7.5) comprising glucose 1.0%, starch 1.0%, peptone 1.0%, meat extract 0.5%, and NaCl 0.5% and cultivated at 32° C. for 24 hours to provide a seed solution. This seed solution was inoculated on a fermentation medium (pH 7.5) comprising bran 3.0%, ammonium sulfate 0.5%, and $CaCO_3$ 0.5% in a proportion of 5% and cultured at 37° C. for 48 hours while aerating and stirring (by the use of a 20 liter-volume Jar Fermentor). After the cultivation was completed, the cultured broth was filtered to obtain a filtrate. The thus-obtained filtrate was cooled, and starch was added thereto in an amount of 1/100 (w/v) of the filtrate. The resulting mixture was stirred at 5° C. for 20 hours to allow the cyclodextrin-synthesizing enzyme to be adsorbed on the starch. Then, the mixture was subjected to centrifugal separation to separate the starch with the enzyme adsorbed thereon. The starch with the enzyme adsorbed thereon was freeze-dried to obtain Enzyme K.

A part of the freeze-dried powder (Enzyme K) was taken, and water was added thereto in an amount of 5/1 (v/w) of the freeze-dried powder. The mixture was stirred for 30 minutes while heating at 50° C. and filtered. The filtrate thus-obtained was again freeze-dried to obtain Enzyme L.

(ii) Male wistar rats (138 to 137 g) (groups of six rats) were deprived of food for 24 hours. At the end of the period, starch was orally administered in an amount of 1 g/kg, and at the same time, Enzymes K and L prepared above were administered, respectively, 30 minutes after the administration, blood samples were collected, and the blood glucose level was determined. The results are shown in Table 6-1.

It can be seen from Table 6-1 that with the group to which Enzyme K or L was administered, the blood glucose level was significantly lowered compared with the control group to which starch alone was administered.

TABLE 6-1

| Group | Blood Glucose Level after 30 Minutes (mg/dl) |
|---|---|
| Control | 175 |
| Group administered with Enzyme K (30 mg/kg) | 134 |
| Group administered with Enzyme L (1 mg/kg) | 129 |

(The value is an average value for each group of six rats.)

(iii) In the same manner as in (ii) above except that 2 g/kg of sucrose was orally administered in place of starch, the effects of Enzyme K and Enzyme L were examined. The results are shown in Table 6-2. As can be seen from Table 6-2, with the group to which Enzyme K or Enzyme L was administered, the blood glucose level was markedly reduced compared with the control group to which only sucrose was administered.

TABLE 6-2

| Group | Blood Glucose Level after 30 Minutes (mg/dl) |
|---|---|
| Control | 172 |
| Group administered with Enzyme K (30 mg/kg) | 141 |
| Group administered with Enzyme L (1 mg/kg) | 138 |

(The blood glucose level is an average value for each group of six rats.)

EXAMPLE 10

(i) A cyclodextrin-synthesizing enzyme-producing strain, Bacillus stearothermophilus IAM 1035, was inoculated on a culture medium (pH 7.5) containing glucose 1.0%, starch 1.0%, peptone 1.0%, meat extract 0.5%, and NaCl 0.5% and aerobically cultivated at 40° C. for 48 hours. After the cultivation was completed, the cultured broth was filtered. The thus-obtained filtrate was cooled, and starch was then added thereto in an amount of 1/100 (w/v) of the filtrate. The resulting mixture was stirred for 12 hours while cooling at 5° C. to allow the cyclodextrin-synthesizing enzyme to be adsorbed on the starch. The starch with the enzyme adsorbed thereon was separated by centrifugal separation and freeze-dried to obtain Enzyme M.

(ii) The blood glucose level-lowering effect of Enzyme M was examined by the same method as in Example 9. With the control group to which starch alone was administered, the blood glucose level after 30 minutes was 170 mg/dl, whereas the blood glucose level of the group to which Enzyme M was administered in an amount of 100 mg/kg was significantly reduced to 137 mg/dl (the values are average values for each group of six rats).

EXAMPLE 11

(i) A dextransucrase-producing strain, Leuconostoc mesenteroides NRRL B-1299, was aerobically cultured on a culture medium (pH 7.4) containing sucrose 2%, corn steep liquor 2%, $K_2HPO_4$ 0.2%, $MgSO_4.7H_2O$ 0.01%, $FeSO_4.7H_2O$ 0.001%, $MnCl_2.4H_2O$ 0.001%, and NaCl 0.001% at 26° C. for 30 hours. After the cultivation was completed, a culture solution was filtered and separated into a filtrate and a cell fraction.

A part of the filtrate was treated in the same manner as in the preparation of Enzyme A in Example 1-(i), whereby Enzyme N was obtained.

(ii) Male ICR mice (18 to 20 g) (groups of five mice) were deprived of food for 24 hours, and sucrose was orally administered in an amount of 2.5 g/kg. At the same time, Enzyme N and a glucosidase-inhibiting agent were orally administered under the conditions shown in Table 7. After 15 minutes and 30 minutes, blood samples were collected, and the blood glucose level was determined. The results are shown in Table 7. When Enzyme N is used in combination with Bay g 5421 (produced by Bayer, West Germany) or Tris (produced by Merk & Co., U.S.A.), the blood glucose lowering effect is increased compared with the cases that Enzyme N, Bay g 5421 and Tris are used separately.

TABLE 7

| Group | Blood Glucose Level (mg/dl) After 15 Minutes | After 30 Minutes |
|---|---|---|
| Control | 269 | 224 |
| Enzyme N (40 mg/kg) | 211 | 195 |
| Bay g 5421 (2 mg/kg) | 208 | 201 |
| Tris (100 mg/kg) | 220 | 209 |

TABLE 7-continued

| Group | Blood Glucose Level (mg/dl) | |
|---|---|---|
| | After 15 Minutes | After 30 Minutes |
| Enzyme N (20 mg/kg) + Bay g 5421 (1 mg/kg) | 166 | 150 |
| Enzyme N (20 mg/kg) + Tris (50 mg/kg) | 171 | 159 |

EXAMPLE 12

(i) A cyclodextrin-synthesizing enzyme-producing strain, Bacillus macerans ATCC 8514, was inoculated on a culture medium (pH 6.5) comprising oatmeal 5%, $(NH_4)_2HPO_4$ 0.3%, $Na_2SO_4$ 0.2%, KCl 0.04%, and small amounts of the chlorides of Mg, Ca, Mn, Fe (trivalent), Zn and Co, and aerobically cultivated at 37° C. for 15 hours. The culture solution was concentrated to 1/10 of the original volume thereof, and an equal amount of acetone was added while cooling. Precipitates formed were collected, dissolved in a small amount of water, and freeze-dried to obtain Enzyme O.

(ii) The blood glucose level-lowering effect of Enzyme O, Bay g 5421, and a combination thereof was examined by the same method as in Example 11 except that 1 g/kg of starch was used in place of the sucrose. The results are shown in Table 8. It can be seen from Table 8 that the effect obtained when Enzyme O and Bay g 5421 are administered at the same time is much greater than that obtained when they are administered separately.

TABLE 8

| Group | Blood Glucose Level (mg/dl) | |
|---|---|---|
| | After 15 Minutes | After 30 Minutes |
| Control | 246 | 203 |
| Enzyme O (50 mg/kg) | 193 | 181 |
| Bay g 5421 (2 mg/kg) | 201 | 178 |
| Enzyme O (25 mg/kg) + Bay g 5421 (1 mg/kg) | 162 | 150 |

EXAMPLE 13

(i) A dextransucrase-producing strain, Streptococcus mutans 6715 (deposited in Kokuritsu Yobo Eisei Kenkyu Jo, Shika Eisei Bu (Tokyo)), was inoculated on a brain heart infusion broth medium (produced by Nippon Seiyaku Co., Ltd.) and cultivated aerobically at 37° C. for 18 hours. The cultured broth was filtered, and the resulting filtrate (960 ml) was adjusted to 60% saturation by adding ammonium sulfate. Precipitates formed were collected, dissolved in a small amount of a physiological saline solution, and dialyzed overnight against the physiological saline solution to obtain Enzyme P (40 ml).

(ii) The blood glucose level-lowering effect of Enzyme P, Bay g 5421, Tris, and combinations thereof was examined by the same method as in Example 11. The results are shown in Table 9. The effect obtained when Enzyme P is used in combination with Bay g 5421 or Tris is much greater than those obtained when they are administered separately.

TABLE 9

| Group | Blood Glucose Level (mg/dl) | |
|---|---|---|
| | After 15 Minutes | After 30 Minutes |
| Control | 255 | 229 |
| Enzyme P (1 ml/kg) | 222 | 201 |
| Bay g 5421 (2 mg/kg) | 215 | 204 |
| Tris (100 mg/kg) | 233 | 216 |
| Enzyme P (0.5 ml/kg) + Bay g 5421 (1 mg/kg) | 169 | 150 |
| Enzyme P (0.5 ml/kg) + Tris (50 mg/kg) | 170 | 161 |

EXAMPLE 14

Male wistar rats (140 to 148 g) (groups of six rats) were deprived of food for 24 hours, and 1 g/kg of starch was orally administered. At the same time, Enzyme K prepared in Example 9 and a glucosidase-inhibiting agent TAI were orally administered under the conditions shown in Table 10. After 30 minutes, blood samples were collected, and the blood glucose level was determined. The results are shown in Table 10. As can be seen from Table 10, the effect obtained by administering Enzyme K and a glucosidase-inhibiting agent TAI in combination was markedly high compared with those obtained by administering Enzyme K and the glucosidase-inhibiting agent TAI separately.

TABLE 10

| Group | Blood Glucose Level after 30 Minutes (mg/dl) |
|---|---|
| Control | 162 |
| Enzyme K (5 mg/kg) | 151 |
| Enzyme K (30 mg/kg) | 133 |
| TAI (0.4 mg/kg) | 148 |
| TAI (2 mg/kg) | 136 |
| Enzyme K (5 mg/kg) + TAI (0.4 mg/kg) | 125 |

| PREPARATION EXAMPLE 1 | |
|---|---|
| Cyclodextrin-synthesizing enzyme (Enzyme L prepared in Example 9) | 50 mg |
| Fine crystalline cellulose | 50 mg |
| Corn starch | 15 mg |
| β-Cyclodextrin | 20 mg |
| Milk sugar | 12 mg |
| Polyvinyl pyrrolidone | 3 mg |
| | (total: 150 mg) |

The cyclodextrin-synthesizing enzyme (Enzyme L in Example 9), fine crystalline cellulose, corn starch, β-cyclodextrin, and milk sugar were mixed, and an aqueous solution of polyvinyl pyrrolidone was added thereto as a binder. The resulting mixture was granulated by a conventional method. These granules were placed in a gelatin-cured capsule to prepare a capsule.

| PREPARATION EXAMPLE 2 | |
|---|---|
| Cyclodextrin-synthesizing enzyme (Enzyme L in Example 9) | 10 mg |
| Glucosidase-inhibiting agent (TAI) | 15 mg |
| Fine crystalline cellulose | 55 mg |
| Corn starch | 24 mg |
| Milk sugar | 20 mg |
| Carboxymethyl cellulose calcium salt | 10 mg |
| Polyvinyl pyrrolidone | 6 mg |
| Talc | 10 mg |

-continued

PREPARATION EXAMPLE 2

(total: 150 mg)

The cyclodextrin-synthesizing enzyme (Enzyme L in Example 9), glucosidase-inhibiting agent TAI, fine crystalline cellulose, corn starch, milk sugar, and carboxymethyl cellulose calcium salt were mixed, and an aqueous solution of polyvinyl pyrrolidone was added thereto as a binder. The resulting mixture was granulated by a conventional method. Then, the talc was added thereto, and the mixture was formed into tablets having a weight of 150 mg.

While the invention has been described in detail and with reference to specific embodiments thereof, it will be apparent to one skilled in the art that various changes and modifications can be made therein without departing from the spirit and scope thereof.

What is claimed is:

1. A method of lowering the blood glucose level in mammals capable of consuming easily-digestible saccharides and which require lowering of blood glucose level, comprising orally administering thereto an effective amount of an enzyme capable of synthesizing sparingly-digestible saccharides from said easily-digestible saccharides.

2. A method as in claim 1, wherein the enzyme is administered together with a glucosidase-inhibiting agent.

3. A method as in claim 1 or 2, wherein the enzyme synthesizes sparingly-digestible polysaccharides or oligosaccharides from easily-digestible monosaccharides, oligosaccharides, or polysaccharides.

4. A method as in claim 1 or 2, wherein the enzyme is at least one member selected from dextransucrase and cyclodextrin-synthesizing enzymes.

5. A method as in claim 4, wherein the dextransucrase is produced by a bacterium selected from the genera Leuconostoc and Streptococcus, and the cyclodextrin-synthesizing enzyme is produced by a bacterium selected from the genera Bacillus and Klebsiella.

6. A method as in claim 1 or 2, wherein the enzyme is dextransucrase produced by a strain belonging to the genus Streptococcus.

7. A method as in claim 1 or 2, wherein the enzyme is a cyclodextrin-synthesizing enzyme produced by a strain belonging to the genus Bacillus.

8. A method as in claim 1, wherein the enzyme is orally administered in an amount of 1 to 100 mg/day.

9. A method as in claim 2, wherein the mixture of the enzyme and the glucosidase-inhibiting agent is orally administered in an amount of 1 to 100 mg/day.

10. A blood glucose level-lowering agent comprising effective amounts of an enzyme capable of synthesizing sparingly-digestible saccharides from easily-digestible saccharides and a glucosidase-inhibiting agent.

11. A blood glucose level-lowering agent as in claim 10, wherein the glucosidase-inhibiting agent inhibits the amylase, sucrase, and maltase actions.

12. A blood glucose level-lowering agent as in claim 10, wherein the weight ratio of the enzyme to the glucosidase-inhibiting agent is from 1/20 to 20/1.

* * * * *